US 8,465,725 B2

(12) United States Patent
Babich et al.

(10) Patent No.: US 8,465,725 B2
(45) Date of Patent: Jun. 18, 2013

(54) PROCESS FOR PRODUCTION OF HETERODIMERS OF GLUTAMIC ACID

(75) Inventors: John W. Babich, Cambridge, MA (US); Craig Zimmerman, Topsfield, MA (US); Kevin P. Maresca, Tewksbury, MA (US)

(73) Assignee: Molecular Insight Pharmaceuticlas, Inc., Cambridge, MA (US)

( * ) Notice: Subject to any disclaimer, the term of this patent is extended or adjusted under 35 U.S.C. 154(b) by 240 days.

(21) Appl. No.: 12/815,637

(22) Filed: Jun. 15, 2010

(65) Prior Publication Data

US 2011/0008253 A1     Jan. 13, 2011

Related U.S. Application Data

(60) Provisional application No. 61/187,120, filed on Jun. 15, 2009.

(51) Int. Cl.
     *A61K 51/00*      (2006.01)
     *A61K 49/00*      (2006.01)

(52) U.S. Cl.
     USPC ............ 424/1.85; 424/9.3; 424/9.1; 514/332; 514/588; 514/595

(58) Field of Classification Search
     USPC ................. 424/1.85, 1.93, 9.1; 562/439, 496, 562/560; 514/332, 588, 595
     See application file for complete search history.

(56) References Cited

FOREIGN PATENT DOCUMENTS
WO    WO-2006/032911    3/2006
WO    WO-2007/008848    1/2007

OTHER PUBLICATIONS

K.P. Maresca et al. A Series of Halogneated Heterodimeric Inhibitors of Prostate Specific Membrane Antigen (PSMA) as Radiolabeled Probes for Targeting Prostate Cancer, J. Med. Chem. 2009, 52, 347-357.*
Ying Chen et al. Radiohalogenated Prostate-Specific Membrane Antigen (PSMA)-Based Ureas as Imaging Agents for Prostate Cancer, J. Med. Chem. 2008, 51, 7933-7934.*
Babich, et al., "Applications of Nuclear Imaging in Drug Discovery and Development," Drug Discovery Dev., 2006, vol. 1, pp. 365-381.
Berthommier, E., et al., "New preparation of [123I]PE2I: investigation of the oxidation and purification steps," J. Label Compd Radiopharm, 2002, vol. 45, No. 12, pp. 1019-1028.
Chen et al., XP009142643 "Radiohalogenated Prostate-Specific Membrane Antigen (PSMA)-Based Ureas as Imaging Agents for Prostate Cancer", Journal of Medicinal Chemistry, vol. 51, 2008, pp. 7933-7943.
Chen, et al., "Age-related decrease in cardiopulomnary andrenergic neuronal function in children as assessed by I-123 metaiodobenzylgucanidine imaging," J. Nucl. Cardiol., 2008, vol. 15, No. 1, pp. 73-79.
Donovan et al., XP002614474 "Fluorous Isocyanates: Convenient Synthons for the Preparation of Radioiodinated Compounds in High Effective Specific Activity", Journal of Organic Chemistry, vol. 74, Oct. 2, 2009, pp. 8133-8138.
Flux, et al., "Absorbed Dose Ratios for Repeated Therapy of Neuroblastoma with I-131 mIBG," Cancer Biother., Radiopharm., 2003, vol. 18, No. 1, pp. 81-87.
Fullerton, et al., "Comparison of Radiohaloanalogues of Meta-Iodobenzylguanidine (MIBG) for a Combined Gene-and Targeted Radiotherapy Approach to Bladder Carcinoma," Med. Chem., 2005, vol. 1, pp. 611-618.
Hayakawa et al., XP-002614476 "Second-Generation Total Synthesis of Haterumalide NA Using B-Alkyl Suzuki-Miyaura Coupling", Organic Letters, vol. 10, No. 9, 2008, pp. 1859-1862.

(Continued)

*Primary Examiner* — Michael G Hartley
*Assistant Examiner* — Jagadishwar Samala
(74) *Attorney, Agent, or Firm* — Gilberto M. Villacorta; Jeffrey R. Lomprey; Foley & Lardner LLP

(57) ABSTRACT

A manufacturing process for the preparation of radiolabeled compounds of formula (I)

(I)

includes reacting compounds of formula (II) with a source of radionuclide of a halogen in the presence of an oxidant under acidic condition, (II)

wherein:
    *I is $^{123}$I, $^{124}$I, $^{125}$I or $^{131}$I;
    R is lower alkyl, optionally substituted with one or more fluorine atoms;
    Q is C(O), O, NR', S, S(O)$_2$, C(O)$_2$, (CH$_2$)$_p$;
    Y is C(O), O, NR', S, S(O)$_2$, C(O)$_2$, (CH$_2$)$_p$;
    R' is H, C(O), S(O)$_2$, C(O)$_2$;
    Z is H, C$_1$-C$_4$ alkyl, benzyl, substituted benzyl or trialkylsilyl;
    m is 0, 1, 2, 3, 4 or 5;
    n is 0, 1, 2, 3, 4, 5 or 6; and
    p is 0, 1, 2, 3, 4, 5 or 6.

28 Claims, 5 Drawing Sheets

OTHER PUBLICATIONS

Maresca et al., XP002614472 "A Series of Halogenated Heterodimeric Inhibitors of Prostate Specific Membrane Antigen (PSMA) as Radiolabeled Probes for Targeting Prostate Cancer", Journal of Medicinal Chemistry, vol. 52, 2009, pp. 347-357.

McIntee, et al., "A Convenient Method for the Preparation of Fluorous Tin Derivatives for the Fluorous Labeling Strategy" J. Org. Chem., 2008, vol. 73, pp. 8236-8243.

International Search Report and Written Opinion for PCT/US2010/038645; mailed Jun. 8, 2011.

Uddin et al., XP-002614475 "Synthesis and evaluation of [123I]-indomethacin derivatives as COX-2 targeted imaging agents", Journal of Labelled Compounds and Radiopharmaceuticals, vol. 52, No. 2, May 2009, pp. 387-393.

\* cited by examiner

PROCESS FOR PRODUCTION OF HETERODIMERS OF GLUTAMIC ACID

CROSS-REFERENCE TO RELATED APPLICATIONS

This application claims the benefit of U.S. Provisional Application No. 61/187,120 filed on Jun. 15, 2009, the contents of which are incorporated by reference herein in their entirety.

TECHNICAL FIELD

This invention relates in general to processes for production of radiolabeled heterodimers of glutamic acid that can be used as therapeutic medicines or as radiopharmaceuticals that enable imaging of tissues.

BACKGROUND

At least 1 million men suffer from prostate cancer and it's estimated that the disease will strike one in six U.S. men between the ages of 60 and 80. There are more than 300,000 new cases of prostate cancer diagnosed each year. Prostate cancer will affect one in six men in the United States, and the mortality from the disease is second only to lung cancer. An estimated $2 billion is currently spent worldwide on surgical, radiation, drug therapy and minimally invasive treatments, $1 billion of the spending in the U.S. There is presently no effective therapy for relapsing, metastatic, androgen-independent prostate cancer. New agents that will enable rapid visualization of prostate cancer and specific targeting to allow radiotherapy present are needed.

Human prostate-specific membrane antigen (PSMA), also known as folate hydrolase I (FOLH1), is a trans-membrane, 750 amino acid type II glycoprotein which is primarily expressed in normal human prostate epithelium but is up-regulated in prostate cancer, including metastatic disease. PSMA is a unique exopeptidase with reactivity toward poly-gamma-glutamated folates, capable of sequentially removing the poly-gamma-glutamyl termini. Since PSMA is expressed by virtually all prostate cancers and its expression is further increased in poorly differentiated, metastatic and hormone-refractory carcinomas, it is a very attractive target for prostate imaging and therapy. Developing ligands that interact with PSMA and carry appropriate radionuclides may provide a promising and novel targeting option for the detection, treatment and management of prostate cancer.

Low molecular weight mimetics, with higher permeability in solid tumors will have a definite advantage in obtaining high percent per gram and a high percentage of specific binding. Molecular Insight Pharmaceuticals is developing radiolabeled small molecules based on the glutamate-urea-lysine heterodimer that target PSMA. In preparation for the radiolabeled compounds, a facile and robust, radiosynthetic production method was developed.

SUMMARY

One aspect of the present invention is directed to processes for the preparation of a radiolabeled compound of the formula (I):

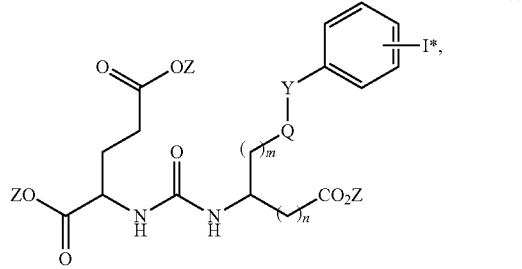

the process including: reacting a compound of formula (II) with a metal salt of *I in the presence of an oxidant under acidic condition,

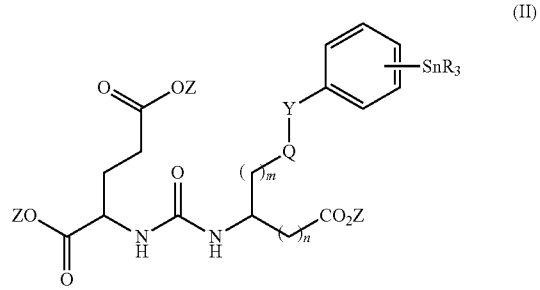

where *I is $^{123}I$, $^{124}I$, $^{125}I$ or $^{131}I$; R is lower alkyl, optionally substituted with one or more fluorides; Q is C(O), O, NR', S, $S(O)_2$, $C(O)_2$, $(CH_2)_p$; Y is C(O), O, NR', S, $S(O)_2$, $C(O)_2$, $(CH_2)_p$; R' is H, C(O), $S(O)_2$, $C(O)_2$; Z is H, $C_1$-$C_4$ alkyl, benzyl, substituted benzyl or trialkylsilyl; m is 0, 1, 2, 3, 4 or 5; n is 0, 1, 2, 3, 4, 5 or 6; and p is 0, 1, 2, 3, 4, 5 or 6.

In some embodiments, the process includes dissolving the metal salt of *I in a base. In some embodiments, the base is NaOH.

In other embodiments, the process also includes reacting a low concentration of a cold metal iodide with the compound of formula (II), the metal salt of *I, and the oxidant. In some such embodiments, the low concentration is from 0.1 to 10 μg of cold metal iodide per 50 mCi of the metal salt of *I. In other embodiments, the cold metal iodide is $Na^{127}I$.

The present invention also provides stable compositions including a radiolabeled compound of the formula (I),

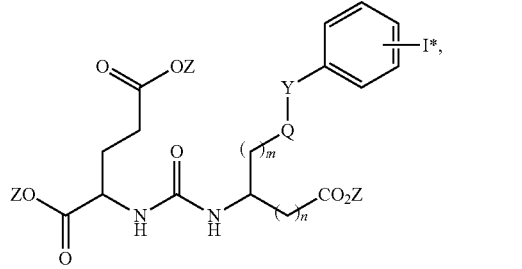

and pharmaceutically acceptable excipients under acidic conditions, where *I is $^{123}I$, $^{124}I$, $^{125}I$ or $^{131}I$; R is lower alkyl, optionally substituted with one or more fluorides; Q is C(O), O, NR', S, $S(O)_2$, $C(O)_2$, $(CH_2)_p$; Y is C(O), O, NR', S, $S(O)_2$, $C(O)_2$, $(CH_2)_p$; R' is H, C(O), $S(O)_2$, $C(O)_2$; Z is H, $C_1$-$C_4$ alkyl, benzyl, substituted benzyl or trialkylsilyl; m is 0, 1, 2, 3, 4 or 5; n is 0, 1, 2, 3, 4, 5 or 6; and p is 0, 1, 2, 3, 4, 5 or 6.

DETAILED DESCRIPTION

Figures 1A, 1B, 1C:
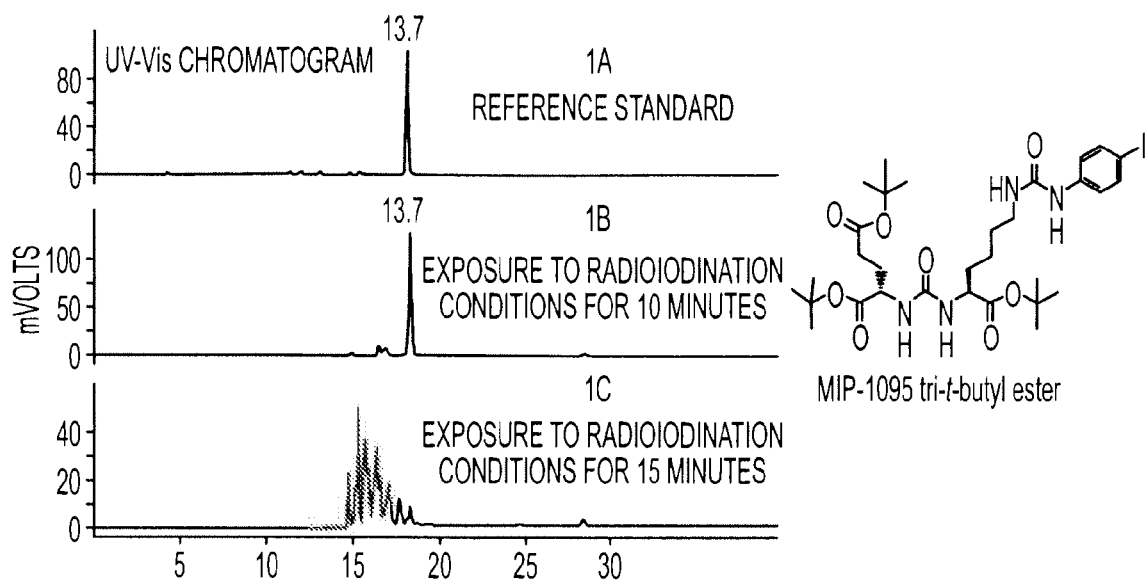
FIGS. 1A-1C are UV-Vis chromatograms respectively of the reference standard (1A), MIP-1095 tri-t-butyl ester exposures to radioiodination conditions for 10 minutes (1B) and exposure for 15 minutes (1C).

The present invention provides processes for the preparation of a radiolabeled compound of the formula (I)

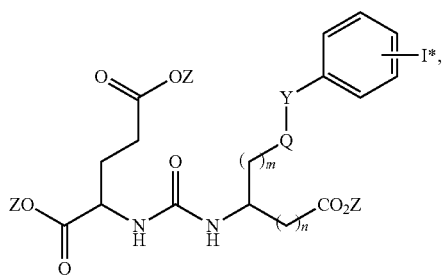

(I)

the process including: reacting a compound of formula (II) with a metal salt of *I in the presence of an oxidant under acidic condition,

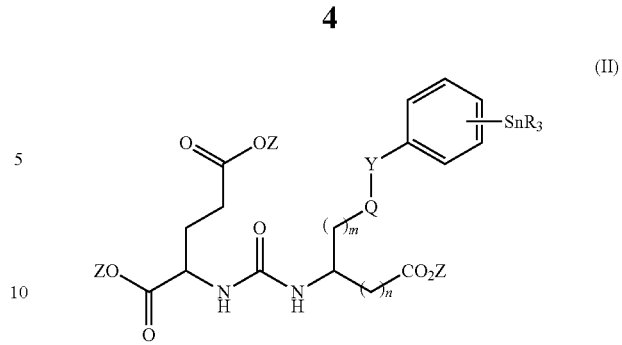

(II)

where *I is $^{123}$I, $^{124}$I, $^{125}$I or $^{131}$I; R is lower alkyl, optionally substituted with one or more fluorides; Q is C(O), O, NR', S, $S(O)_2$, $C(O)_2$, $(CH_2)_p$; Y is C(O), O, NR', S, $S(O)_2$, $C(O)_2$, $(CH_2)_p$; R' is H, C(O), $S(O)_2$, $C(O)_2$; Z is H, $C_1$-$C_4$ alkyl, benzyl, substituted benzyl or trialkylsilyl; m is 0, 1, 2, 3, 4 or 5; n is 0, 1, 2, 3, 4, 5 or 6; and p is 0, 1, 2, 3, 4, 5 or 6. In some embodiments, R is a $C_1$-$C_4$ alkyl that is optionally substituted with one or more fluorine atoms. In some embodiments, R is methyl, ethyl, or propyl. In some embodiments, Q is $(CH_2)_p$. In some embodiments, Z is $C_1$-$C_4$ alkyl. In some embodiments, Z is tert-butyl. In some embodiments, Q is $(CH_2)_p$, p is 4 and m is 0. In some embodiments, n is 0.

In a preferred embodiment, the acidic condition has pH of less than about 3. In another preferred embodiment, R is methyl for the preparation of a radiolabeled compound of the formula (I). In another preferred embodiment, the metal salt is a Group IA metal salt of *I where *I is $^{123}$I, $^{124}$I, $^{125}$I or $^{131}$I. In some embodiments, the metal salt is a metal salt of $^{123}$I or $^{131}$I. In some embodiments, the metal salt is a sodium salt. In some embodiments, the metal salt is a sodium salt of $^{123}$I or $^{131}$I. In yet another preferred embodiment, the oxidant includes peracid; preferable peracetic acid.

Initially, the synthesis of the radioiodine labeled compounds following known literature procedures starting with the trimethylstannyl precursors resulted in a low radiochemical yield (RCY) and reduced binding in vitro. In accordance with the present invention, the key factors for process improvement include lower pH reaction conditions, the proper order of addition of reagents, the proper oxidant and efficient purification methods. In order to achieve high RCY, it is important to maintain reaction conditions ≦pH 3, preferably at pH 1-3. For example, when pH was 5.5, the RCY for [$^{123}$I]MIP-1095 tri-t-butyl ester was about 30% while if pH was 2, the RCY increased greatly to about 80% (See scheme 1).

Scheme 1: Effect of pH for Iododestannylation

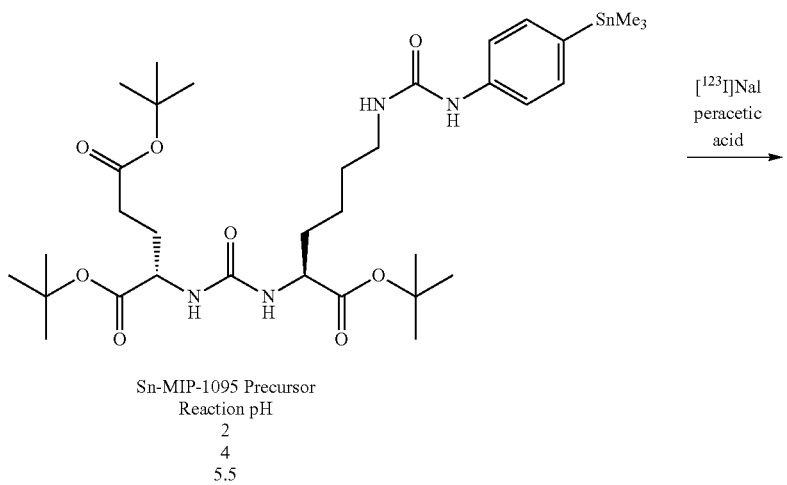

Sn-MIP-1095 Precursor
Reaction pH
2
4
5.5

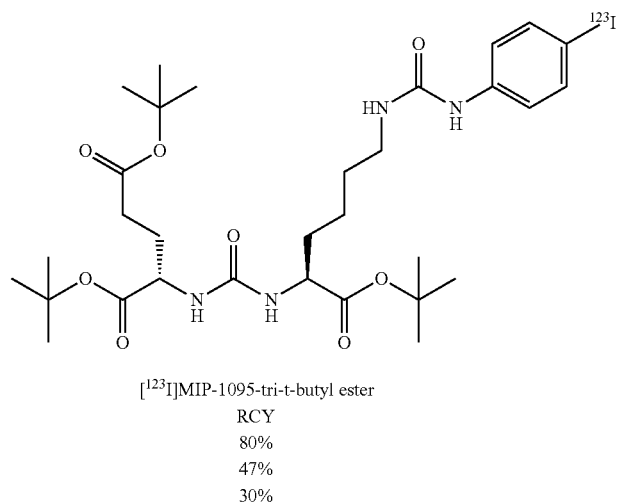

[123I]MIP-1095-tri-t-butyl ester
RCY
80%
47%
30%

The amount of acetic acid added prior to the addition of the oxidant is deemed critical and the additional acid such as sulfuric acid may be added to compensate for the increased volume of sodium hydroxide present in the incoming radioactive Na*I. The processes are carried out under acidic conditions. The optimized pH is deemed to be less than about 3; preferably pH=1-3. Thus, in accordance with the present invention, an acid is added prior to the addition of the oxidant in the process of stannylation reaction. In the related embodiment, the acid includes mineral or organic acid. The mineral acid is a non-halogen bearing or releasing acid. In a preferred embodiment, the acid includes phosphoric acid, sulfuric acid, acetic acid, and the like. The amount of acid added is sufficient to maintain pH 1-3.

In some embodiments, a "cold" metal iodide may be added to the reaction in low concentration in addition to the metal salt of *I. As used herein, a "cold" metal iodide refers to a metal iodide having low radioactivity. In some embodiments, a "cold" metal iodide refers to a metal $^{127}$I salt. In some embodiments, the cold metal iodide is Na$^{127}$I. The low concentration of the cold metal iodide in the sodium hydroxide solution ranges from 0.1 to 10 μg of Na$^{127}$I per 50 mCi of metal Na*I. In some embodiments, the low concentration of the cold metal iodide in the sodium hydroxide solution ranges from 0.1 to 2 μg of Na$^{127}$I per mCi of metal Na*I. In some embodiments, the low concentration of the cold metal iodide in the sodium hydroxide solution is about 1 μg of Na$^{127}$I per mCi of metal Na*I. Such "spiking" of the Na*I with the cold metal iodide may increase the RCY to greater than 75%, according to some embodiments. According to other embodiments, the spiking results in a RCY of greater than 80%, 85%, or 90%. In some embodiments, the spiking results in a RCY of from 80% to 95%.

The trialkyltin compound of formula (II) can be prepared by the conversion of its halogen precursor directly or indirectly or by other suitable methods known in the art. For example, compound 3 can be prepared by reductive amination from an amine compound 1 with trimethyltin benzaldehyde 2. The direct conversion of the iodide-4 to the trimethyltin compound 5 can be realized via palladium catalyzed stannylation reaction (Scheme 2). Furthermore, fluorous tagging compounds of formula (II) where R is fluoride substituted lower alkyl can be purified via fluorous purification techniques known in the art. The convenient methods for the preparation of fluorous aryl stannes were reported previously, see for example, McIntee, et. al., "A Convenient Method for the Preparation of Fluorous Tin Derivatives for the Fluorous Labeling Strategy" *J. Org. Chem.* 2008, 73, 8236-8243.

Scheme 2: Exemplary routes to the compounds of formula (II)

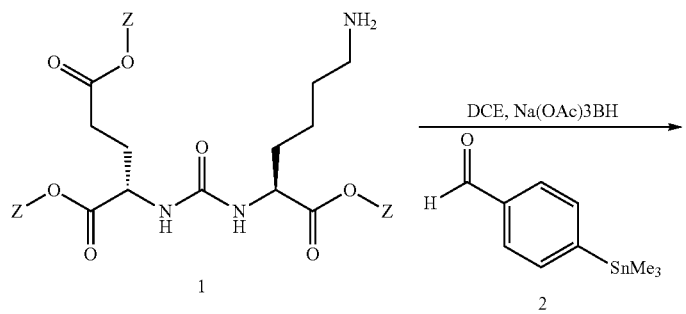

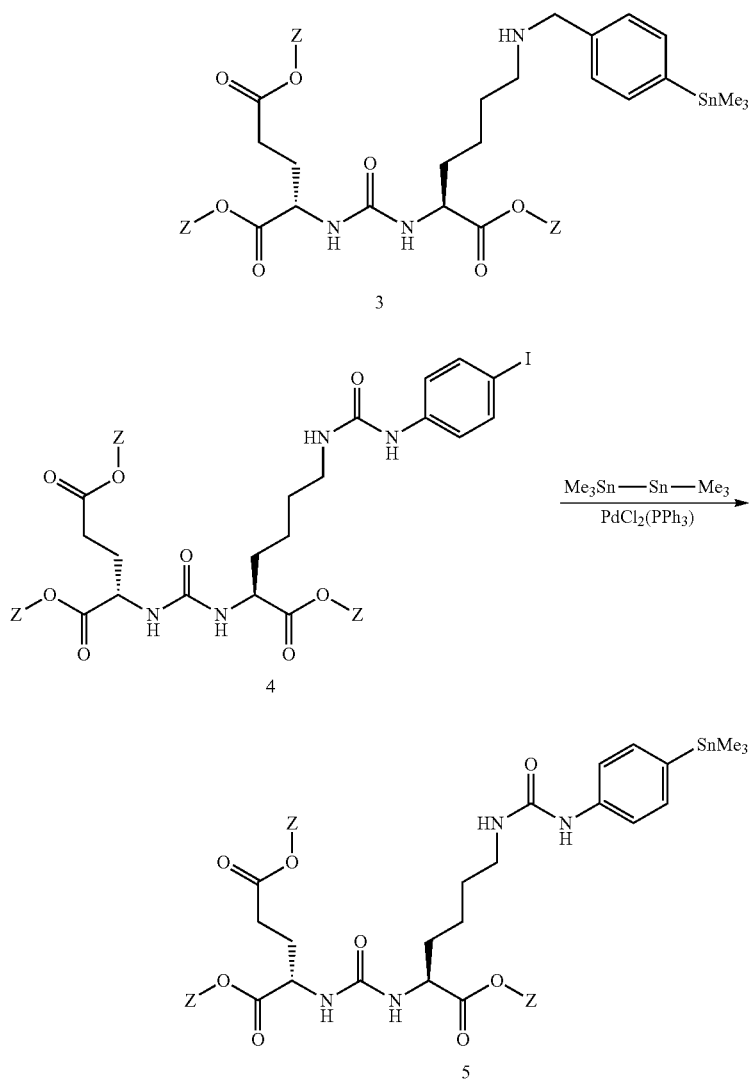

Figures 2A, 2B, 2C:
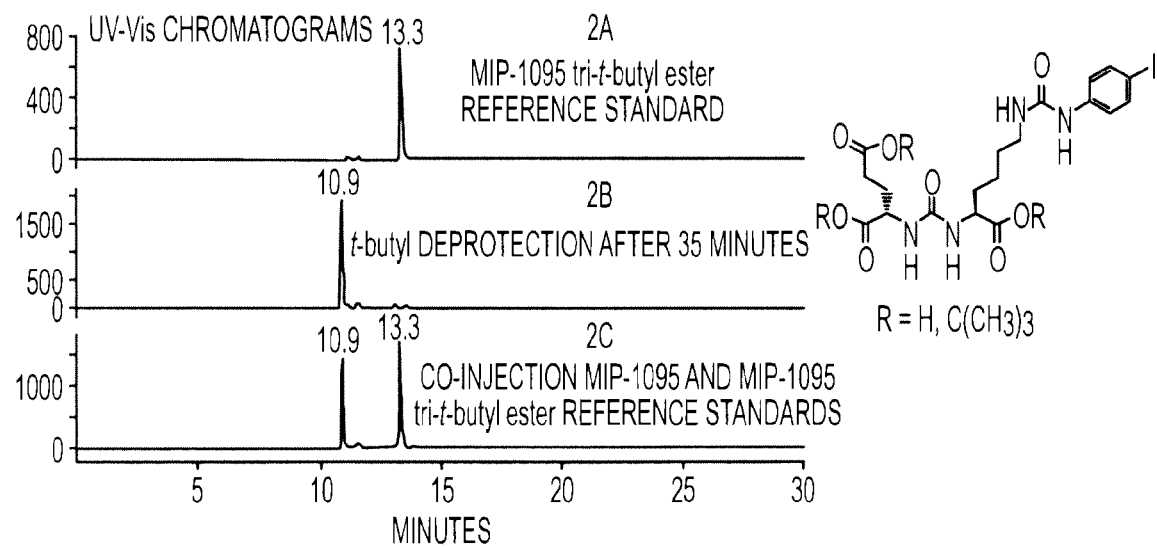
FIGS. 2A-2C show effect of reaction time of MIP-1095 tri-t-butyl ester after 35 minutes under deprotection condition.

In accordance with the present invention, a suitable carboxylic acid protection group is required to achieve a high radiochemical yield (RCY). Suitable carboxylic acid protection groups are those protecting groups that can withstand acidic conditions. On the other hand, if the protecting group is very inert, then the harsh conditions and/or prolonged reaction time are needed to de-protect the carboxylic acid functional group. Such harsh conditions may result in the loss of radioactivity. Thus, in accordance with the present invention, the carboxylic acid protecting group is preferably $C_1$-$C_4$ alkyl, benzyl, substituted benzyl or trialkylsilyl. For example, the carboxylic acid protecting group may be t-butyl, 4-dimethoxybenzyl, 4-methoxybenzyl, 4-nitrobenzyl, 2,4-dinitrobenzyl, benzyl, trimethylsilyl, triethylsilyl, or the like. Such protecting groups can withstand acidic conditions for short time periods (e.g. 10 minute) under acidic conditions, and can easily be de-protected without prolonged reaction times. For instance, when Z is t-butyl, it was determined that prolonged reaction times (e.g. >10 min) of iododestannylation would deprotect one or more of the t-butyl ester protecting groups of [$^{123}$I]MIP-1095-tri-t-butyl ester leading to low RCY. See FIGS. 1A-1C. After a fast purification, deprotection of t-butyl ester of $^{123}$I-MIP-1095 (Z=t-butyl) was determined to be completed (Z=H) within a short time for about 30 to 50 minutes. See exemplary FIGS. 2A-2C. In a similar manner, one of skilled in the art would find other suitable carboxylic acid protecting groups in accordance with the practice of the present invention.

In another embodiment, the compound of formula (I) in the processes is

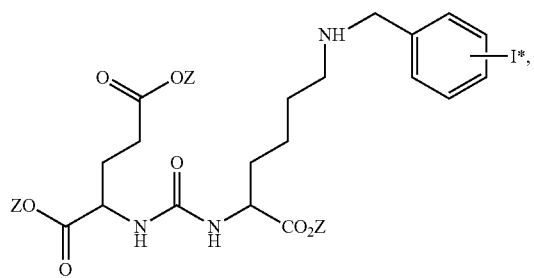

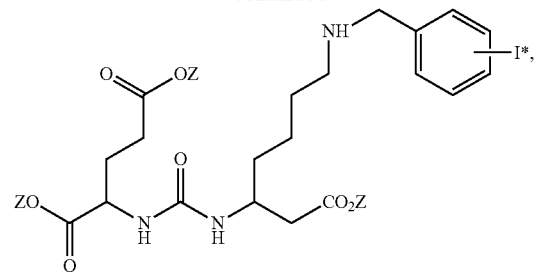
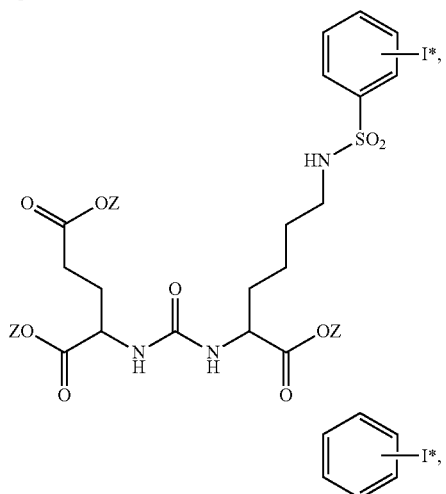
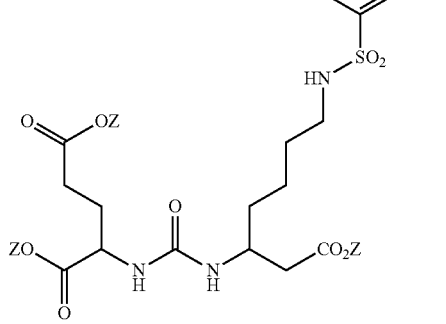
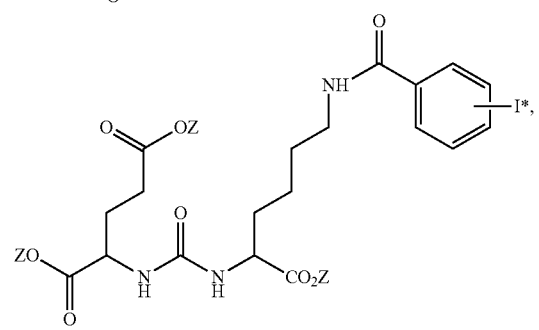
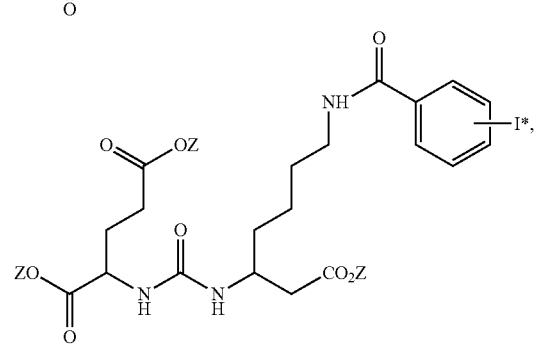
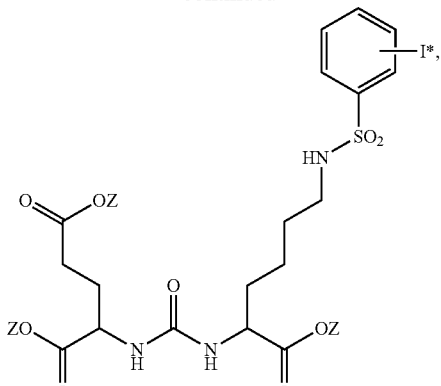
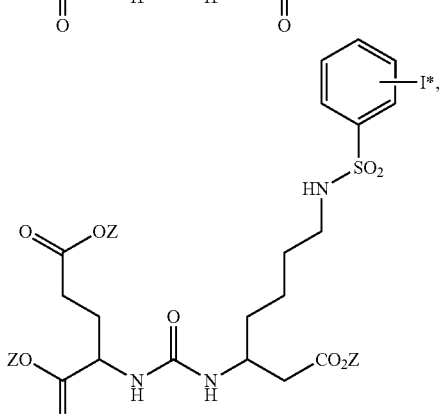
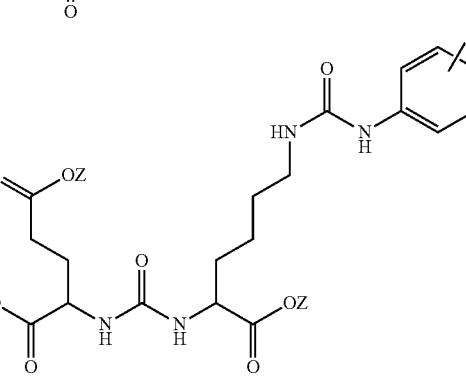
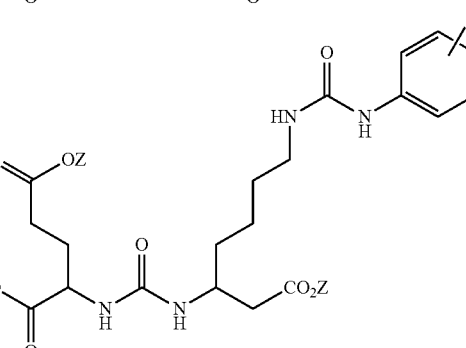
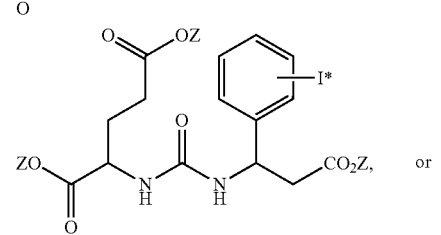

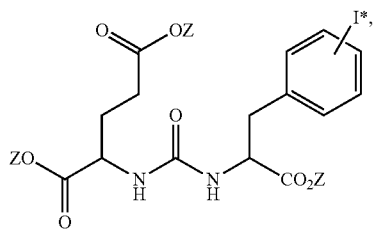

where *I is $^{123}$I, $^{124}$I, $^{125}$I or $^{123}$I; and Z is H, $C_1$-$C_4$ alkyl, benzyl, substituted benzyl or trialkylsilyl, provided the compound of formula (I) is not

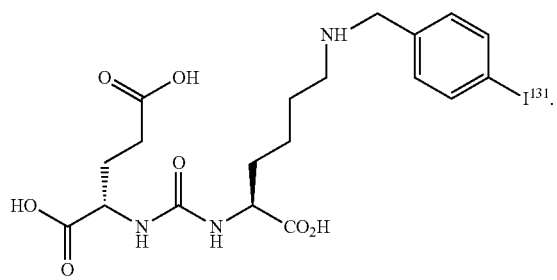

In accordance with the present invention, compounds that contain an aryl iodide moiety, hold significant potential as radiopharmaceuticals, e.g. for imaging ($^{123}$I-labeled) and therapy ($^{131}$I-labeled) of PSMA positive prostate cancer. Iodine-123, with its relatively short half-life (13.2 h) and 159 keV γphotons, is an ideal radionuclide for imaging by single-photon emission computed tomography (SPECT). Babich, et al., *Drug Discovery Dev.* 2006, 1, 365-381; Chen, et al., *J. Nucl. Cardiol.* 2008, 15, 73-79. On the other hand, iodine-131, with an 8 day half-life and both γ and β emissions, offers the potential for therapy. Fullerton, eta al., *Med. Chem.* 2005, 1, 611-618; Flux, et al., *Cancer Biother, Radiopharm.* 2003, 18, 81-87. In a preferred embodiment, the compounds of formula (I) include the radioisotope of iodine (*I) having a half-life of 13.2 hours or less. In another embodiment, the compounds of formula (I) include iodine-123.

In a preferred embodiment, the compound of formula (I) in the process is

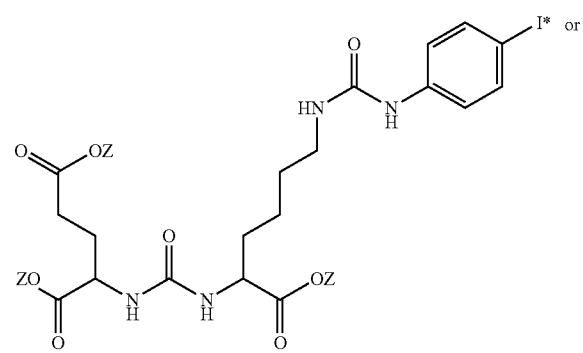

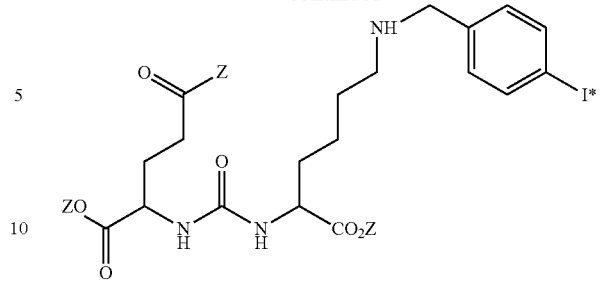

where *I is $^{123}$I or $^{131}$I; and Z is H, $C_1$-$C_4$ alkyl, benzyl, substituted benzyl or trialkylsilyl, provided the compound of formula (I) is not

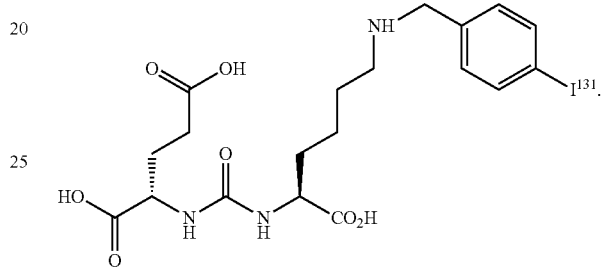

In another preferred embodiment, the compound of formula (I) in the process is

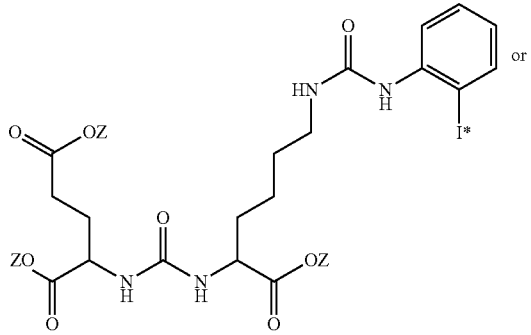

where *I is $^{123}$I or $^{131}$I; and Z is H, $C_1$-$C_4$ alkyl, benzyl, substituted benzyl or trialkylsilyl.

In another embodiment, the present invention provides a compound of formula (II) according to the process for the preparation of a radiolabeled compound of the formula (I). In a preferred embodiment, the compound is

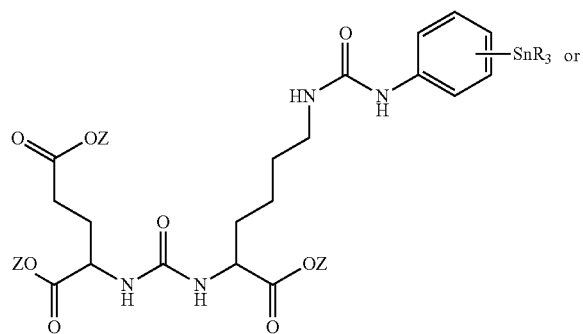

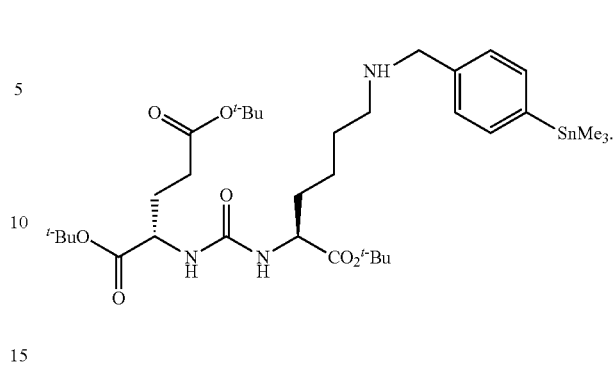

provided the compound is not

Specifically, the compound is

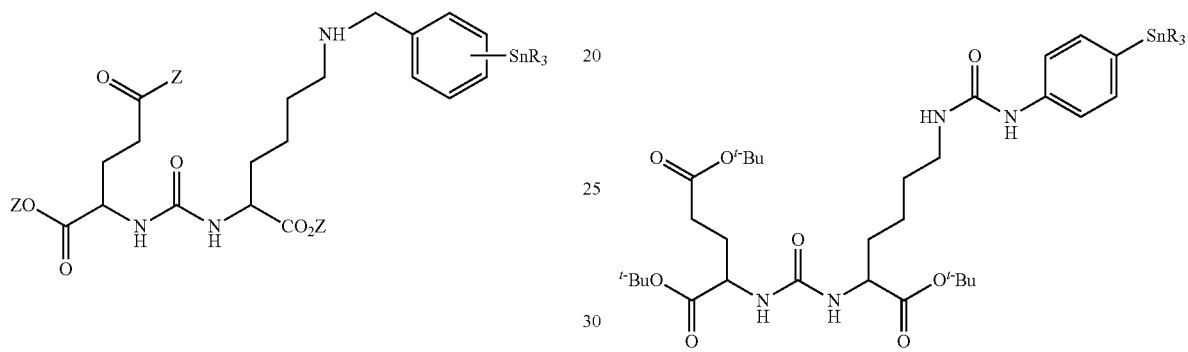

where R is lower alkyl, optionally substituted with one or more fluorides, and Z is H, $C_1$-$C_4$ alkyl, benzyl, substituted benzyl or trialkylsilyl. In a more preferred embodiment, the compound is

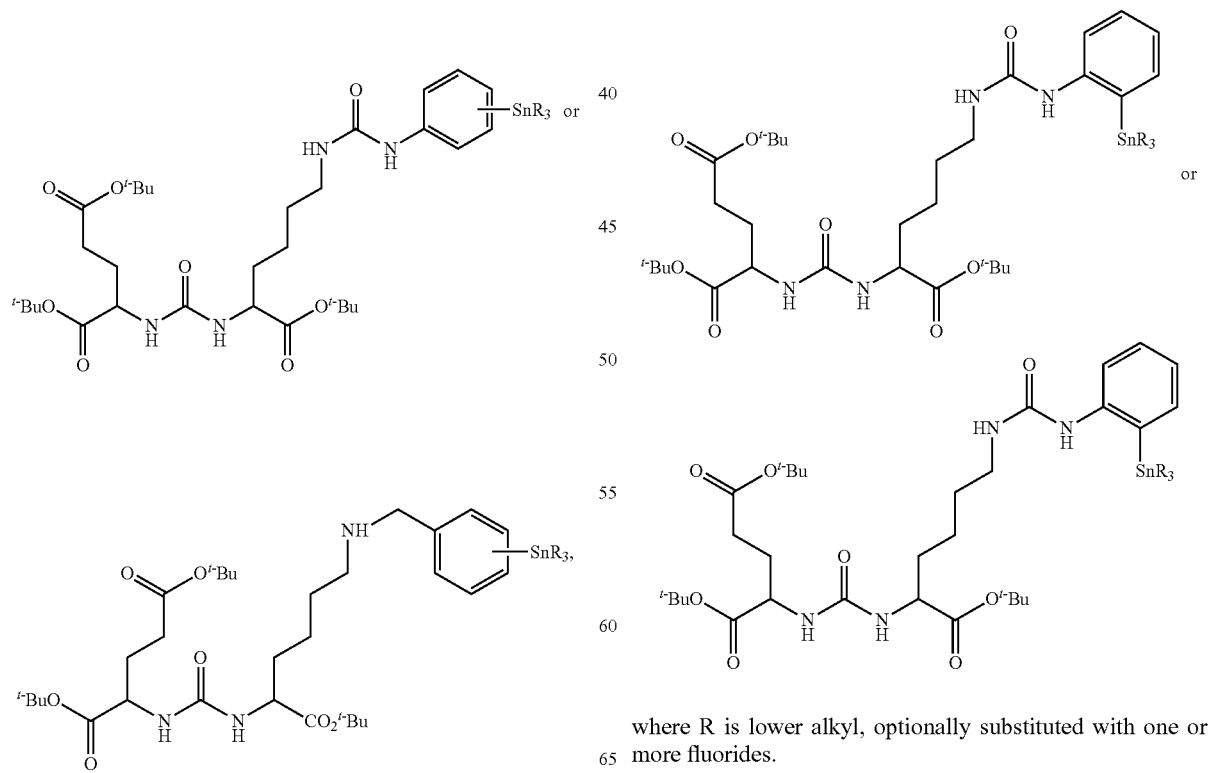

where R is lower alkyl; alternatively, the compound may be where R is lower alkyl, optionally substituted with one or more fluorides.

In another preferred embodiment, benzyl ester protected compounds such as

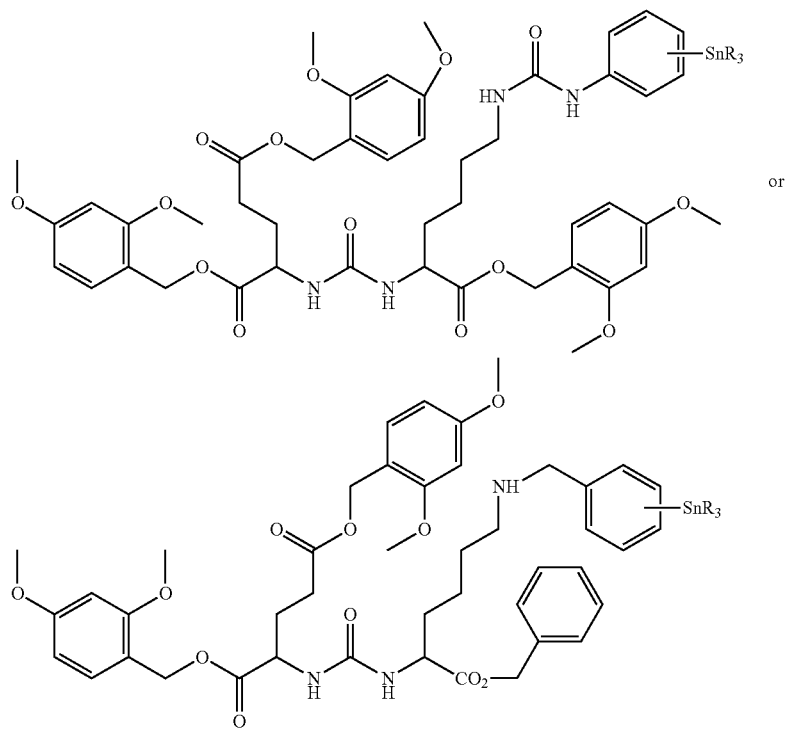

may be used in the process for the preparation of a compound of formula (I).

"Alkyl" refers to a straight-chain, branched or cyclic saturated aliphatic hydrocarbon. Typical alkyl groups include methyl, ethyl, propyl, isopropyl, butyl, isobutyl, tertiary butyl, pentyl, hexyl and the like. The alkyl group may be optionally substituted with one or more substituents selected from the group consisting of hydroxyl, cyano, halogen or alkoxy. A lower alkyl is an alkyl group with 1 to 6 carbons.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino. Examples of aryl groups include phenyl, naphthyl and anthracyl groups. Phenyl and substituted phenyl groups are preferred.

"Heteroaryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl, and the like.

"Carboxylic acid protecting groups" refer those groups that one skilled in the art would recognize as being suitable to protect the carboxylic acid (—COOH) substituent on an alkyl or ringed system as described herein and which may be removed under deprotection conditions known to those skilled in the field as set forth. Suitable carboxyl protecting groups include but are not limited to amides e.g. 5,6-dihydrophenathridinamide, hydrazides e.g. N-phenylhydrazides and carboxylic acid esters e.g. t-butyl esters, substituted ethyl esters, aryl esters, substituted or unsubstituted benzyl esters e.g., 2,4-dimethoxybenzyl esters, silyl esters e.g., trimethylsilyl, and the like. Protecting groups may be removed by any suitable condition such as acid or base catalyzed hydrolysis or catalytic hydrogenolysis. Where the carboxylic acid is protected as a benzyl ester, the protecting group may be removed, for example, by hydrogenolysis or other suitable means. Where the carboxylic acid is protected as a t-butyl ester, the protecting group may be removed, for example, by hydrolysis with trifluoroacetic acid or other suitable means. Where appropriate protecting groups will be chosen to ensure they can be selectively removed.

In another embodiment, the processes also include a chromatography purification step to obtain a radiolabeled compound of the formula (I). In a related embodiment, the chromatographic purification step includes high pressure liquid chromatography.

The chromatographic purification step may also include reverse phase column chromatography; for example, C18 solid phase cartridge (e.g. C18 Sep Pak) may be used as a facile way to remove free iodine, inorganic salts and other minor organic side products to reproducibly produce the desired product in excellent radiochemical purity.

The present invention also provides stable compositions including a radiolabeled compound of the formula (I), and pharmaceutically acceptable excipients under acidic conditions. In a preferred embodiment, the stable compositions include a radiolabeled compound of the formula (I), an ascorbate/asorbic acid; and a stabilizing amount of a gentisate stabilizer selected from gentisic acid and the soluble, pharmaceutically-acceptable salts in pH 4.5 to 5.5 thereof.

The present technology, thus generally described, will be understood more readily by reference to the following examples, which are provided by way of illustration and are not intended to be limiting.

EXAMPLE

General Methods

All reactions were carried out in dry glassware under an atmosphere of argon unless otherwise noted. Reactions were purified by column chromatography under medium pressure using a Biotage SP4 or by preparative high pressure liquid chromatography using a Varian Prostar 210 preparative HPLC system equipped with a semi-preparative Vydac C18 reverse-phase column (250 mm×10 mm×5 μm) connected to a Varian Prostar model 320 UV-visible detector and monitored at a wavelength of 254 nm unless otherwise noted. Analytical HPLC of the radioiodinated compounds may be performed using the same method with an analytical Vydac C18 reverse-phase column (250 mm×4.6 mm×5 μm). Elemental analysis was performed by Prevalere Life Sciences, Inc. High-resolution mass spectra were determined by M-Scan Inc. using positive ion electrospray with a Q-Tof API US hybrid quadrupole/time-of-flight mass spectrometer.

$^1$H NMR was recorded on a Bruker 400 MHz instrument. Spectra are reported as ppm δ and are referenced to the solvent resonances in CDCl$_3$, DMSO-d$_6$ or methanol-d$_4$. All solvents were purchased from Sigma-Aldrich. Reagents were purchased from Sigma Aldrich, Bachem, Akaal, Fisher, Alfa Aesar, Acros and Anaspec. The following abbreviations are used methylene chloride (DCM), ethyl acetate (EA), hexanes (Hex), dichloroethane (DCE), dimethyl formamide (DMF), trifluoroacetic acid (TFA), tetrahydrofuran (THF), carbonyldiimidazole (CDI), dimethylaminopyridine (DMAP), triethylamine (TEA), methyl trifluoromethanesulfonate (MeOTf), (S)-2-Amino-6-(bis-pyridin-2-ylmethyl-amino)-hexanoic acid (dpK), glutamic acid (Glu), diisopropylethylamine (DIEA), benzyloxycarbonyl (CBZ).

General Radiochemistry.

All reactions were carried out in a laboratory designed and licensed for use of radioactivity. All iodine isotopes were purchased from MDS Nordion as Na*I in mild sodium hydroxide solutions or in dry form concentrated from aqueous sodium hydroxide unless otherwise noted. All solvents (JT Baker) were purchased from Fisher Scientific. The radioiodinated compounds may be purified on a Varian Prostar 210 HPLC system using an analytical Vydac C18 column (250 mm×4.6 mm×5 μm) connected to a Varian Prostar model 320 UV-visible detector monitoring at 254 nm or by C18 Sep Pak Plus column or other suitable systems as noted herein.

Example 1

Synthesis of $^{123}$I-MIP-1072 Trimethylstannane Radiolabeling Precursor $^{123}$I-MIP-1072 is synthesized from the trimethylstannane critical intermediate 7 as described in the experimental procedures below. The synthesis utilizes a high yielding reductive alkylation reaction of the critical intermediate 6 with 4-(trimethylstannyl)benzaldehyde (2).

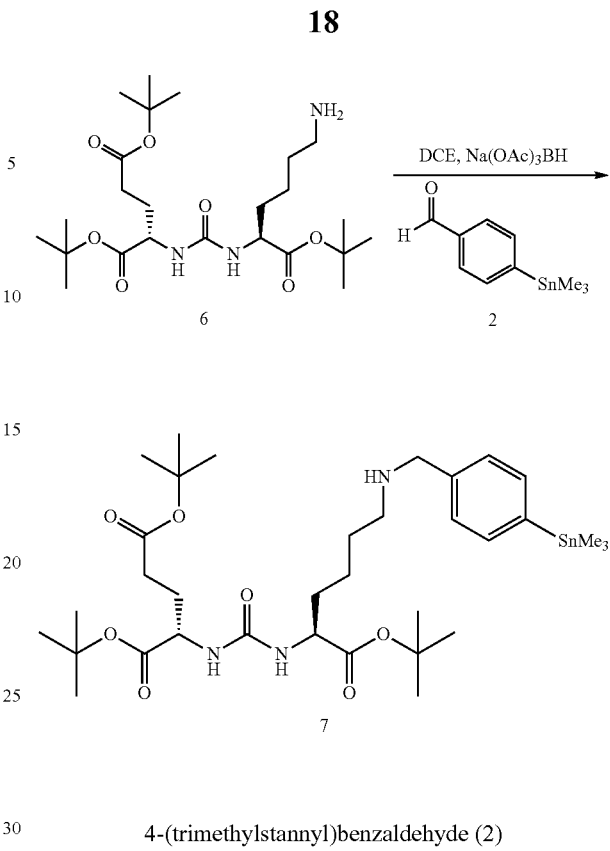

4-(trimethylstannyl)benzaldehyde (2)

To a solution of 4-iodobenzaldehyde (1.92 g, 8.27 mmol) in dry dioxane (60 mL) was added hexamethylditin (4.1 mL, 19.8 mmol) followed by Pd(Ph$_3$P)Cl$_2$ (150 mg) and the reaction mixture was heated for 3 h under reflux until judged complete. The reaction was filtered through celite and purified by column chromatography using hexanes/ethyl acetate (9/1) as eluent to afford (2.24 g, 98%) as a clear oil. $^1$H NMR (400 MHz, CDCl$_3$) δ 9.97 (s, 1H), 7.81 (d, J=7.8 Hz, 2H), 7.72 (d, J=7.8 Hz, 2H), 0.29 (s, 9H). ESMS m/z: 268 (Sn-cluster).

(S)-di-tert-butyl 2-(3-((S)-1-tert-butoxy-1-oxo-6-(4-trimethylstannyl)benzylamino)hexane-2-yl)ureido) pentanedioate (7)

(S)-di-tert-2-(3-((S)-6-amino-1-tert-butoxy-1-oxohexan-2-yl)ureido)pentanedioate (6) (4.7 g, 0.92 mmole) was dissolved in anhydrous dichloroethane (200 mL). 4-(trimethylstannyl)benzaldehyde (2.6 g, 9.7 mmol) and sodium triacetoxyborohydride (3.07 g, 14.5 mmol, 1.5 equivalents) were added sequentially. The reaction mixture was heated to 40° C. under nitrogen for 18 hours after which time a check of the reaction mixture showed complete consumption of the aldehyde. The dichloroethane was removed in vacuo and the product was purified by flash chromatography on a SiO$_2$ column eluted with acetone to give 7, 3.14 g (42%). $^1$H NMR (400 MHz, DMSO-d$_6$) δ 7.48 (d, J=7.4 Hz, 2H), 7.30 (d, J=7.4 Hz, 2H), 6.27 (m, 2H, NH's), 3.96 (m, 4H), 2.74 (bm, 2H), 2.21 (m, 2H), 1.87 (m, 2H), 1.65-1.19 (m, 7H), 1.35 (m, 27H, t-Bu's), 0.23 (s, 9H). ESMS m/z: 742 (Sn-cluster).

Example 2

Radiolabeling Procedure for the Synthesis $^{123}$I—(S)-2-(3-((S)-1-carboxy-5-(4-iodobenzylamino)pentyl)ureido)pentanedioic Acid ($^{123}$I-MIP-1072)

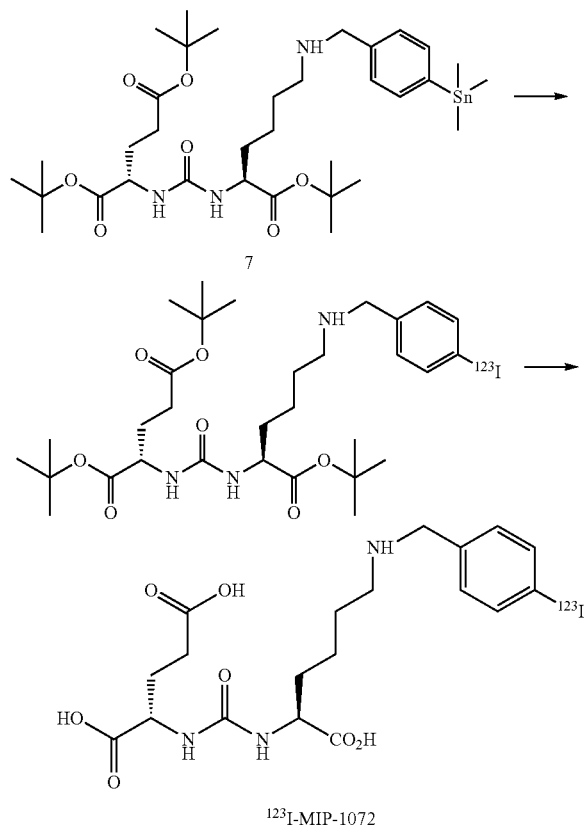

$^{123}$I-MIP-1072

Into a 5 mL vial containing [$^{123}$I]NaI (300 mCi) was added 100 μL of sterile water for injection (SWFI), followed by 305 μL of an acid solution [acetic acid (300 μL) and sulfuric acid (5 μL)], followed by 300 μL of oxidant [acetic acid (0.2 mL) and 30% hydrogen peroxide (0.335 mL) brought to a final volume of 5 mL with SWFI], to which was added 150 μL of (S)-di-tert-butyl 2-(3-((S)-1-tert-butoxy-1-oxo-6-(4-(trimethylstannyl)benzylamino)hexan-2-yl)ureido)pentanedioate (7) (1 mg/mL solution in ethanol). The mixture was vortexed for 2 min and allowed to incubate at room temperature for an additional 30 min. The reaction was quenched with 200 μL of 0.1 M sodium thiosulfate. The product was then diluted in 18 mL of SWFI and loaded onto a C18 Sep Pak Plus column. The column was washed with 60 mL of SWFI to remove unreacted radioiodine and inorganic and organic salts. The $^{123}$I—(S)2-(3-((S)-1-carboxy-5-(4-iodobenzylamino)pentyl)ureido)pentanedioic acid ester was eluted from the column using 6 mL of ethanol. The resulting solution, containing the ester of $^{123}$I-MIP-1072, was evaporated to dryness under a stream of nitrogen and the residue dissolved in DCM (0.5 mL). TFA (2 mL) was added to remove the ester protecting groups. The solution was then incubated at room temperature for 40 min. After the deprotection was complete, the solution was evaporated to dryness under a stream of nitrogen and the residue was dissolved in the formulation matrix of 2% gentisate and 5% ascorbate, pH 5. The radiochemical yields ranged from 50% to 70%, RCP>90%, specific activity of ≧4000 mCi/μmol.

Similarly, $^{131}$I-MIP-1072 can be prepared from the corresponding [$^{131}$I]NaI under the same procedure.

Example 3

Spiking of the Radioiododestannylation

Addition of "cold" sodium iodide (Na$^{127}$I), i.e. "spiking", demonstrates a significant increase in RCY when added to the "hot" sodium iodide solution in NaOH (0.1 M). The increase in RCY was observed with the use of both Nordion's dry Na$^{123}$I and GE Healthcare's Na$^{123}$I (aq.), as the starting $^{123}$I source. These spiking experiments were performed using a range of "cold" NaI (0.1, 0.25, 0.5, 1, 2, 5, 8 and 10 μg per 50 mCi of sodium iodide-123), as indicated in Table 1, below.

TABLE 1

A summary of the "cold" sodium iodide spiking experiments.

| Amount of "cold" sodium iodide added | mCi | % RCY | I-123 NaI source |
|---|---|---|---|
| 20 μg | 100 | 89 | Nordion |
| 10 μg | 50 | 91 | Nordion |
| 8 μg | 400 (50 mCi/μg) | 87 | GE Healthcare |
| 7 μg | 2 (0.25 mCi/μg) | 92 | Nordion |
| 5 μg | 50 | 89 | Nordion |
| 2 μg | 50 | 89 | Nordion |
| 1 μg | 50-60 (55 mCi/μg) | 85 (n = 2) | Nordion |
| 0.5 μg | 48-52 (100 mCi/μg) | 81 (n = 2) | Nordion |
| 0.25 μg | 25 | 79 | Nordion |
| 0.1 μg | 50 | 64 | Nordion |

The results demonstrate that using as little as 0.25 μg Na$^{127}$I/50 mCi of Na$^{123}$I produces significant increases in RCY over control samples where no Na$^{127}$I was used. The controls average a RCY of about 66%. The results also demonstrate an optima of about 1 μg of "cold sodium" iodide per 50 mCi of Na$^{123}$I.

Example 4

Scale up of Radioiododestannylation to Form $^{123}$I-MIP-1072

Results from the development project have demonstrated that scale up to a 250 mCi reaction can be accomplished with minor modifications to the reaction conditions developed in research. The crucial changes investigated were order of addition, pH monitoring, reaction temperature (room temperature or heating) and methods of purification. The desired product could be synthesized in overall 50% radiochemical yield (RCY) reproducibly with only minor variation observed with the yield. The final formulation of 6% ascorbate/3% gentisate afforded a stable formulated solution that contained very little free iodine, free iodine values <5% at time of manufacture (TOE) at room temperature. Using the C18 Sep Pak (SP) proved adequate in removing any free iodine and inorganic salts.

The optimization was developed with the purpose of scale up of the process from the original 5-50 mCi level to 250-300 mCi. Several parameters were investigated: a) the order and amount of Sn-precursor and other reagents b) pH with respect to the amount of I-123 added c) amount of peroxide d) behavior of the C18 SP for purification.

The order of addition was investigated in order for the reaction to be performed directly in the 5 mL vial in which the 1-123 NaI from Nordion arrives. This was successfully achieved allowing for a faster, easier, and safer reaction condition for the production of MIP-1072.

The amount of Sn-precursor was increased from 50 to 150 μg in order to maintain a sufficient excess of precursor and to compensate for the increase in reaction volume balanced with the thought of the final Specific Activity of the product.

The radioiododestannylation reaction will take place efficiently over a wide range of pH, however, the reaction slows down at higher alkaline values. The amount of acetic acid added prior to the addition of the oxidant/acetic acid solution was increased to 0.3 ml with 5 ul of sulfuric acid due to the increased volume of sodium hydroxide solution containing the higher amounts of Na$^{123}$I. The pH during the process was lowered to 1-3 whereas in the past it was maintained in the 4-5 pH range with 0.1 M sodium dihydrogen phosphate. The pH was kept more consistent leading to a more consistent yield of the MIP-1072 product. The optimized pH was determined to be pH=1-3.

The C18 Sep Pak column was employed as a facile way to ensure the purification of the free iodine and produce >97% RCP of the doses. The C18 SP Plus performed quite well in preparing a high purity product with minimal losses.

The experiments demonstrated adequate and reproducible yields for the production process with the batch size scaled-up to 250 mCi. The yields in this experimental series ranged from 17 to 86%. It is suggested that C18 SP Plus column performance be evaluated on a batch to batch basis prior to use in the MIP-1072 manufacturing process.

Verification Batches.

A total of 3 batches were completed and the ranges of the results summarized below in Table 2.

TABLE 2

Summary of verification batches.

| | |
|---|---|
| pH range of final product | 4.5-5.5 |
| RCP at TOM | 97-99% |
| Yield after purification with C18SP | 40-74% |
| Specific Activity at TOC | 500-1000 mCi/μmol |
| RCP at TOC | 87-95% |
| Free Iodine at TOM | 1.0-3.0 ng |
| Vials possibly dispensed | Up to 7 vials per batch |

Stability Results:

Stability was evaluated for up to 2 days at room temperature by quantitation of free I-123 content present by HPLC. The stability was determined at room temperature in an attempt to accelerate any product degradation to more rapidly assess the effectiveness of each radioprotectants in the formulation matrix. The stability studies demonstrated that an increase in free iodine of 3-5% per day could occur when stored at room temperature.

Overall, five full activity experiments were conducted and a number of tracer experiments during this phase of the project. The following highlights the results from these runs.
  a) A 250 mCi process scale up with order of addition altered was completed with modifications to the process with successful production of product.
  b) The 6% ascorbate/3% gentisate formulation continued to show good stability.
  c) The purification of the product could be achieved at the 250 mCi scale with the use of the C18 Sep Pak (Waters).

Example 5

Synthesis of $^{123}$I-MIP-1095 Trimethylstannane Radiolabeling Precursor $^{123}$I-MIP-1095 may be synthesized from the trimethylstannane intermediate 9 which can be prepared as described in the experimental procedure below.

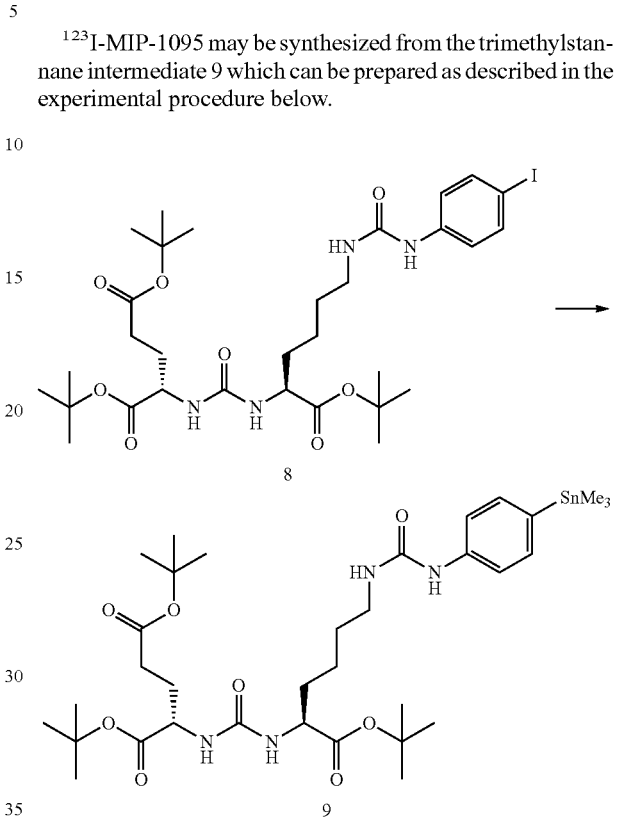

(S)-di-tert-butyl 2-(3-((S)-1-tert-butoxy-1-oxo-6-(4-trimethylstannyl)benzylamino)hexan-2-yl)ureido)pentanedioate (9)

To a solution of 8 (14.8 g, 30.4 mmol) in dichloromethane (500 mL) and triethylamine (3.07 g/4.23 mL, 30.4 mmol) was added 4-iodophenylisocyanate (7.45 g, 30.4 mmol) and the reaction stirred at ambient for 4 h. It was evaporated to dryness and the residue dissolved in methanol (100 mL) and added dropwise to water (900 mL) with stirring. A white solid precipitated and TLC on Merck SiO$_2$ 5714 developed in dichloromethane: methanol (9:1, v/v) indicated material co-eluting with reference standard. It was filtered, washed with water and dried under high vacuum to give (9), 20.82 grams. The crude isolated material (S)-di-tert-2-(3-((S)-1-tert-butoxy-6-(3-(4-iodophenyl)ureido)-1-oxohexan-2-yl)ureido) pentanedioate (9) (13.36 g, 18.27 mmol) was dissolved in anhydrous dioxane (325 mL). Hexamethylditin (9.45 mL, 14.9 g, 45 mmol) was added in one portion at room temperature. The mixture was degassed and backfilled with nitrogen three times. Dichlorobis(triphenylphospnine)palladium(II) (1.34 g, 10 wt % of (I)) was added quickly in one portion and the entire mixture was again degassed and backfilled three times. The temperature was raised to 110° C. and stirred for 1.5 h. TLC analysis on Merck SiO$_2$ 5714 developed in ethyl acetate:hexane (40:60, v/v) indicated complete disappearance of starting material. The reaction mixture was cooled to room temperature and the dioxane was removed in vacuo. The residue was dissolved in dichloromethane and filtered through a pad of celite. It was reduced in volume and applied to a silica flash column (4"×10") and eluted with DCM. The relevant fractions were combined and evaporated to dryness. Further impure fractions containing product were evaporated to dryness and re-purified by flash chromatography on a SiO$_2$ column (4"×10") eluted with ethyl acetate:hexane (1:2, v/v). Relevant fractions were combined and evaporated to dryness. The two products from the column purification were combined and recrystallized from warm ether:heptane (approx 1:2, v/v, 60 mL). The product was filtered, washed with heptane and dried under high vacuum to give (9), weight=8.35 g, yield 62%. $^1$H NMR (400 MHz, DMSO-d$_6$) δ 8.37 (s, 1H), 7.5 (dd, 4H), 6.3 (t, 2H), 6.04 (t, 1H), 4.00 (m, 2H), 3.05 (m, 2H), 2.24 (m, 2H), 1.9 (m, 1H), 1.64 (m, 2H), 1.55 (m, 2H), 1.38 (s, 27H), 1.28 (m, 3H), 0.20 (t, 9H). $^{13}$C NMR (75 MHz, DMSO-d$_6$) δ 173.3, 173.0, 172.5, 156.2, 153.9, 139.6, 136.2, 119.2, 83.0, 52.2, 51.5, 39.8, 31.9, 30.0, 29.6, 27.6, 22.8. ESMS m/z: 771 (M+H)$^+$.

Example 6

Radiolabeling Procedure for the Synthesis $^{123}$I—(S)-2-(3-((S)-1-Carboxy-5-(3-(4-iodophenyl)ureido) pentyl)ureido)pentanedioic Acid ($^{123}$I-MIP-1095)

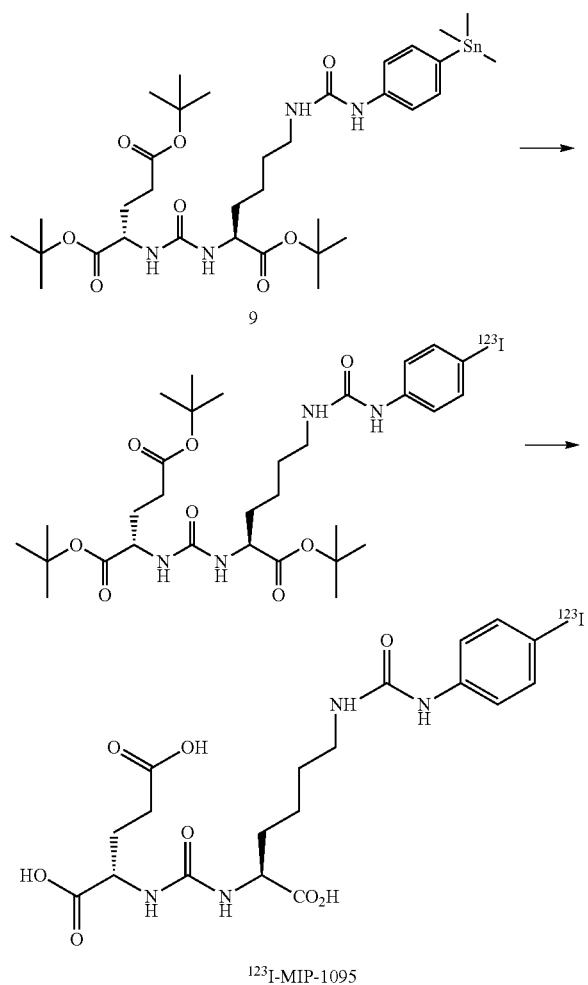

In a 5 mL vial containing [$^{123}$I]NaI (300 mCi) was added sterile water for injection (SWFI) (50 μL), 50% sulfuric acid in SWFI (50 μL), oxidant (100 μL) (which was prepared fresh via the incubation of acetic acid (0.2 mL) and 30% hydrogen peroxide (0.335 mL) followed by dilution to a final volume of 5 mL with SWFI), acetonitrile (0.5 mL), and (S)-di-tert-butyl 2-(3-((S)-1-tertbutoxy-1-oxo-6-(3-(4-(trimethylstannyl)phenyl)ureido)hexan-2-yl)ureido)pentanedioate (9) (100 μL of a 1 mg/mL solution in acetonitrile). The mixture was vortexed for 1 min and allowed to incubate at room temperature for an additional 10 min. The reaction was quenched with 200 μL of 0.1 M sodium thiosulfate. The C18 Sep Pak Plus column. The column was washed with 60 mL of SWFI to remove unreacted radioiodine and inorganic and organic salts. The $^{123}$I—(S)-2-(3-((S)-1-carboxy-5-(3-(4-iodophenyl)ureido)-pentyl)ureido)pentanedioic acid ester was eluted from the column using 4 mL of ethanol. The resulting solution, containing the tri-tert-butyl ester of $^{123}$I-MIP-1095, was evaporated to dryness under a stream of nitrogen. The residue was dissolved in DCM (0.5 mL), and TFA (2 mL) was added to cleave the tert-butyl ester protecting groups. The deprotection solution was incubated at room temperature for 45 min. After the deprotection was complete, the solution was evaporated to dryness under a stream of nitrogen. The product was dissolved in 50% acetonitrile/water and purified on a C18 Sep Pak Plus column using a gradient of SWFI containing 0.1% acetic acid and ethanol, and the product was obtained upon elution with 4 mL of 100% ethanol. The solution was evaporated to dryness under a stream of nitrogen, and the residue was dissolved in a formulation matrix of 2% gentisate and 5% ascorbate/ascorbic acid, pH 5. The radiochemical yields ranged from 50% to 70%, RCP>90%, specific activity of ≥4000 mCi/μmol.

Similarly, $^{131}$I-MIP-1095 can be prepared from the corresponding [$^{131}$I]NaI under the same procedure.

Figures 3A, 3B:
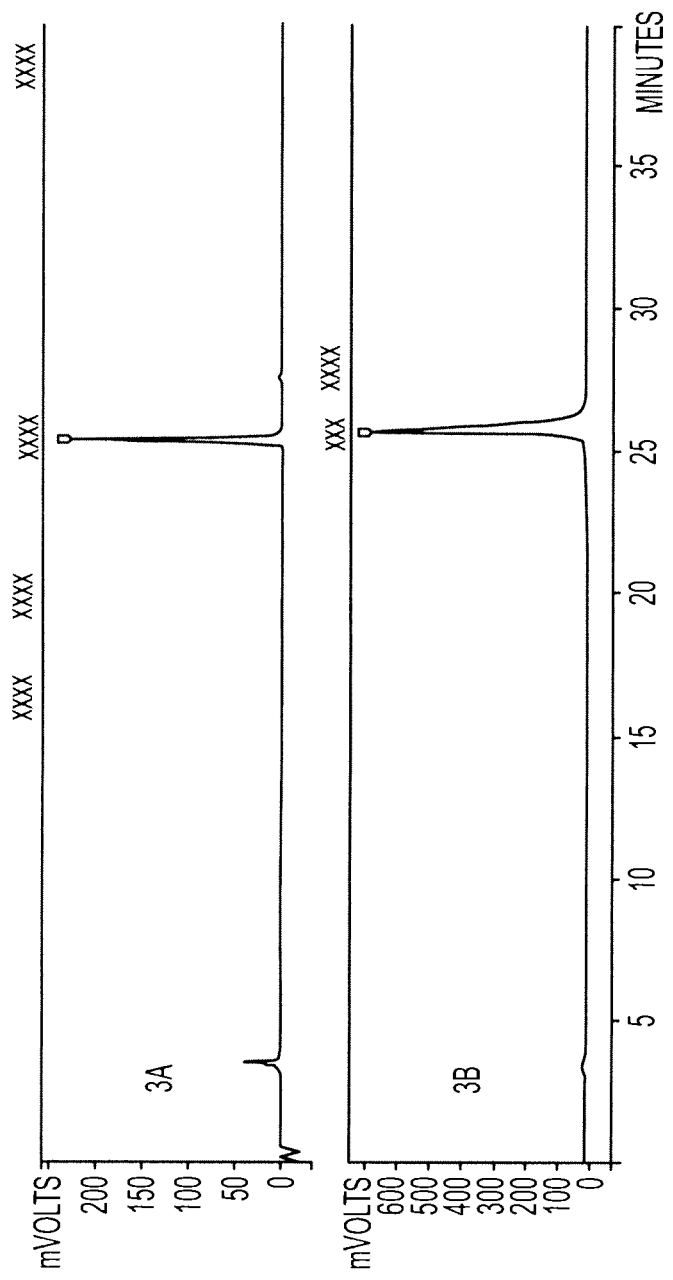
FIG. 3A-3B shows UV-visible chromatogram (3A) and radiochromatogram (3B) of MIP-1095 after RP-HPLC purification demonstrating >95% RCP of the eluted product, upon co-injection.

The identities of the radioiodinated products were confirmed by RP-HPLC through correlation of the retention time of the radioiodinated products with that of the corresponding non-radioiodinated material following co-injection, as shown for MIP-1095 in FIGS. 3A-3B.

Example 7

Scale up of Radioiododestannylation to Form $^{123}$I-MIP-1095

The reaction was developed with the purpose of scaling the process up from the 5-50 mCi level to 250 mCi. Several parameters were considered with respect to the process scale up including a) the order and amount of Sn-precursor, reaction solvent (solubility) and other reagents b) pH with respect to the amount of I-123 added c) amount of and preparation of the oxidant d) behavior of the C18 SP for purification.

The order of addition was investigated in order for the reaction to be performed directly in the 5 mL vial in which the I-123 NaI from Nordion arrived. The possibility of performing the reaction in the incoming vial would eliminate a transfer step, making the process easier and safer while increasing yields by eliminating potential early process losses.

The amount of precursor resin was ranged from 50 to 150 μg in order to maintain a sufficient excess of precursor and to compensate for the increase in reaction volume balanced with the thought of the final Specific Activity of the product.

The radioiododestannylation reaction will take place efficiently over a wide range of pH, however, the reaction yields are lower at higher alkaline values. The amount of acid added prior to the addition of the oxidant/acetic acid solution was increased with additional 25 ul of sulfuric acid (due to the increased volume of sodium hydroxide solution containing the higher amounts of incoming NaI I-123). The pH during the process was lowered to 1-2 whereas in the past it was maintained in the 4-5 pH range with 0.1 M sodium dihydrogen phosphate.

Figure 4:
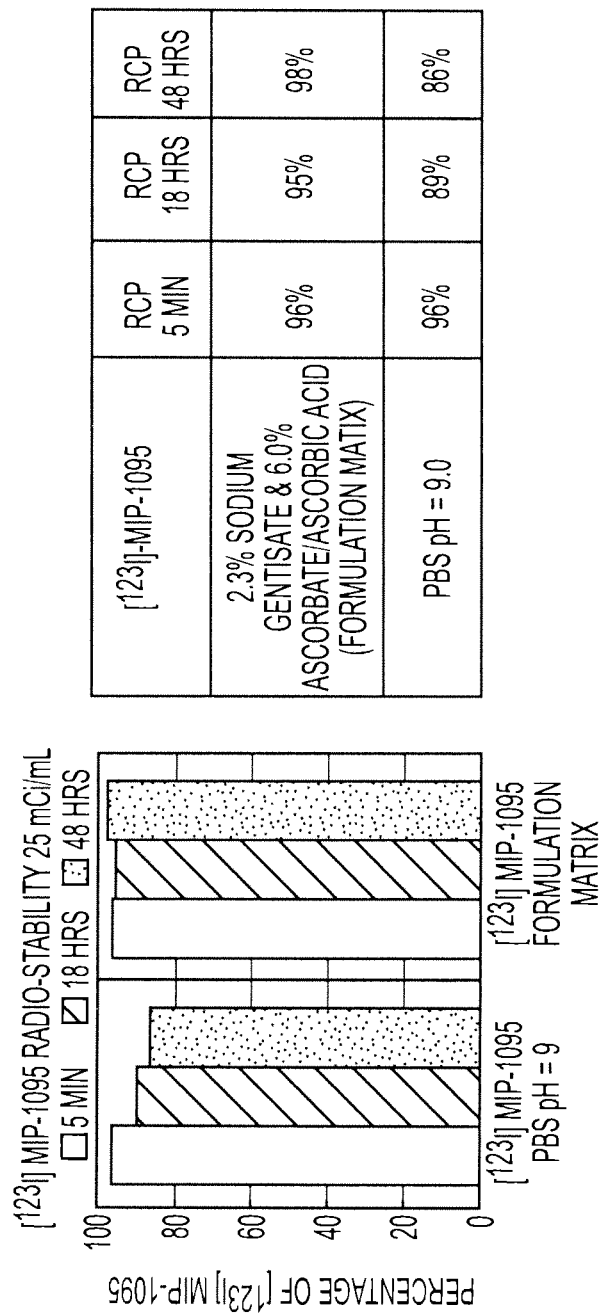
FIG. 4 shows stability profile of the final formulation of 6% sodium ascorbate/ascorbic acid with 2.3% sodium gentisate in sterile water for injection v. formulation of PBS (pH=9.0) at room temperature.

In a 5 mL vial containing [$^{123}$I]NaI was added sterile water for injection (SWFI) (50 µL), 50% sulfuric acid in SWFI (50 µL), oxidant (100 µL) (which was prepared fresh via the incubation of acetic acid (0.2 mL) and 30% hydrogen peroxide (0.335 mL) followed by dilution to a final volume of 5 mL with SWFI), acetonitrile (0.5 mL), and the trimethylstannane precursor, Sn-MIP-1095 (compound 9) (100 µL of a 1 mg/mL solution in acetonitrile). The mixture was vortexed for 1 min and allowed to incubate at room temperature for an additional 10 minutes. The reaction was quenched with 200 µL of 0.1 M sodium thiosulfate. The product was then diluted in 18 mL of SWFI and loaded onto a C18 Sep Pak Plus column. The column was washed with 60 mL SWFI to remove unreacted radioiodine and inorganic and organic salts. The Sn-MIP-1095 precursor and $^{123}$I-MIP-1095 ester are retained on the column. $^{123}$I-MIP-1095 ester was eluted from the column using 4 mL of ethanol, while the Sn-MIP-1095 precursor was retained on the column. The resulting solution, containing the $^{123}$I-MIP-1095 ester, was evaporated to dryness under a stream of nitrogen and the residue was dissolved in methylene chloride (0.5 mL) and TFA (2 mL) was added to remove the ester protecting groups. The deprotection solution was incubated at room temperature for 45 minutes. After the deprotection was complete, the solution was evaporated to dryness under a stream of nitrogen. The product was dissolved in 50% acetonitrile/water and purified on a C18 Sep Pak Plus column using a gradient of SWFI+0.1% acetic acid and ethanol, finally eluting the product with 4 mL of 100% ethanol. The solution was evaporated to dryness under a stream of nitrogen and the residue was dissolved in the formulation matrix of 2-3% Gentisate and 5-7% Ascorbate, pH=5. The radiochemical yields ranged from 50-70%. The final product was filtered through a sterile 0.2 µm Millipore Millex GV (33 mm) filter to yield the final product in >90% RCP with specific activities ≧4000 mCi/µmol. The final formulation of 6% sodium ascorbate/ascorbic acid with 2.3% sodium gentisate in sterile water for injection shows a stable profile compared to formulation of PBS (pH=9.0) at room temperature. See FIG. 4.

Figures 5A, 5B:
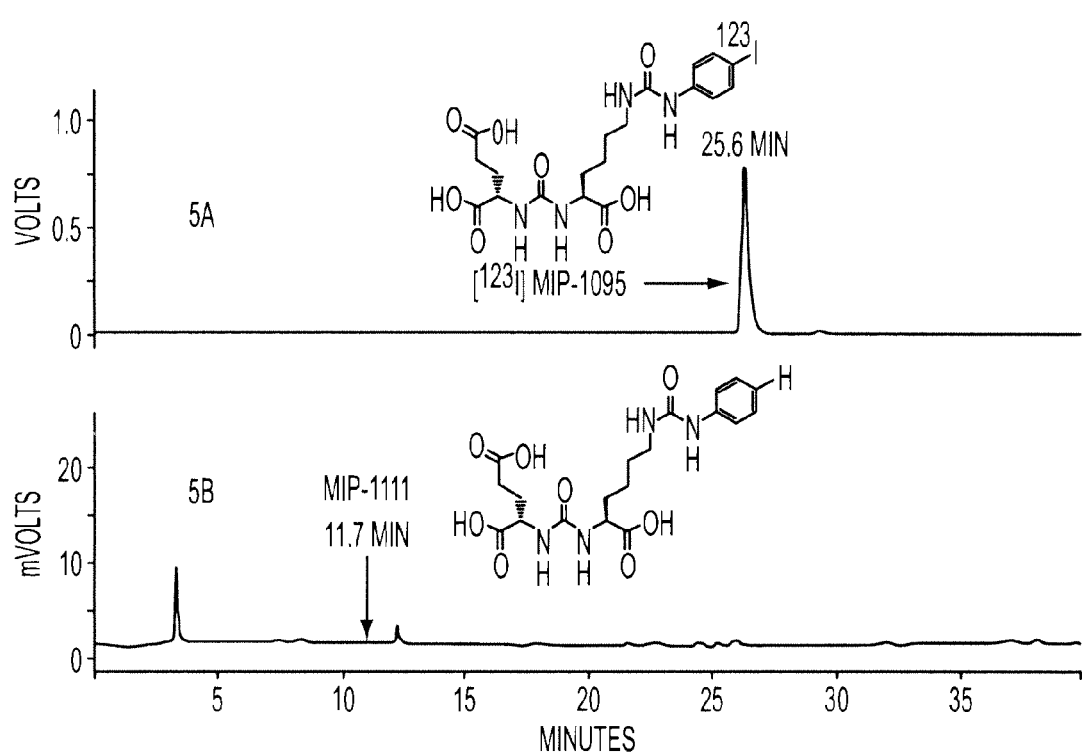
FIGS. 5A-5B are respective HPLC chromatograms of $^{123}$I MIP-1095 and MIP-1111 after double C18 Sep Pak purification.

The C18 Sep Pak purification was demonstrated as a facile way to remove free iodine, inorganic salts and other minor organic side products to reproducibly produce the desired product in excellent radiochemical purity (RCP>97%). FIGS. 5A-5B demonstrate a satisfied result after double C18 Sep Pak purification. Analysis for residual tin containing species (inorganic and organic), residual solvents (methylene chloride and TFA) were performed to ensure the levels are within the required specifications. The specific activity of the product was routinely determined as to ensure that the required specific activity was obtained.

The following exemplary manufacturing flow diagram is provided in accordance with the practice of the present invention:

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

The use of the terms "a" and "an" and "the" and similar referents in the context of describing the elements (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential to the practice of the invention.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Additionally the phrase "consisting essentially of" will be understood to include those elements specifically recited and those additional elements that do not materially affect the basic and novel characteristics of the claimed invention. The phrase "consisting of" excludes any element not specifically specified. In addition, where features or aspects of the disclosure are described in terms of Markush groups, those skilled in the art will recognize that the disclosure is also thereby described in terms of any individual member or subgroup of members of the Markush group.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A process for the preparation of a radiolabeled compound of formula (I)

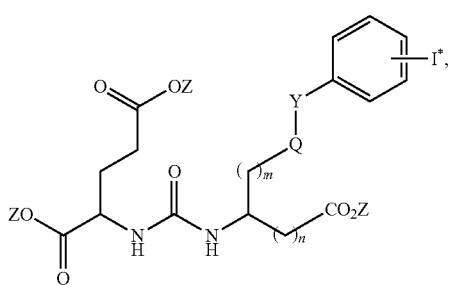
(I)

the process comprising:
reacting a compound of formula (II) with a metal salt of *I in the presence of an oxidant under acidic conditions,

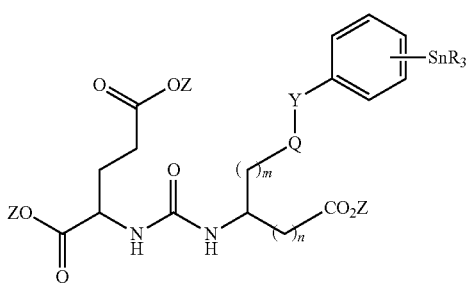
(II)

wherein
*I is $^{123}$I, $^{124}$I, $^{125}$I or $^{131}$I;
R is lower alkyl, optionally substituted with one or more fluorides;
Q is C(O), O, NR', S, S(O)$_2$, C(O)$_2$, (CH$_2$)$_p$;
Y is O, NR', S, S(O)$_2$, C(O)$_2$, (CH$_2$)$_p$;
R' is H, C(O), S(O)$_2$, C(O)$_2$;
Z is H, C$_1$-C$_4$ alkyl, benzyl, substituted benzyl or trialkylsilyl;
m is 0, 1, 2, 3, 4 or 5;
n is 0, 1, 2, 3, 4, 5 or 6; and
p is 0, 1, 2, 3, 4, 5 or 6.

2. The process of claim 1, wherein the acidic conditions comprise a pH of less than about 3.

3. The process of claim 1, wherein R is methyl.

4. The process of claim 1, wherein the metal salt of *I is a Group IA metal salt of *I wherein *I is $^{123}$I, $^{124}$I, $^{125}$I or $^{131}$I.

5. The process of claim 4, wherein the metal salt is a sodium salt.

6. The process of claim 1, wherein the oxidant comprises a peracid.

7. The process of claim 1, wherein the reacting comprises adding an acid to the compound of formula (II) and metal salt of *I, prior to adding the oxidant.

8. The process of claim 7, wherein the acid comprises a mineral acid or an organic acid.

9. The process of claim 8, wherein the mineral acid is a non-halogen bearing or releasing acid.

10. The process of claim 8, wherein the acid comprises phosphoric acid, sulfuric acid or acetic acid.

11. The process of claim 8, wherein an amount of the acid is sufficient to maintain a pH of from 1 to 3.

12. The process of claim 1 further comprising reacting a low concentration of a cold metal iodide with the compound of formula (II), the metal salt of *I, and the oxidant.

13. The process of claim 12, wherein the low concentration is from 0.1 to 10 µg of cold metal iodide per 50 mCi of the metal salt of *I.

14. The process of claim 13, wherein the cold metal iodide is Na$^{127}$I.

15. The process of claim 1, wherein the compound of formula (I) is:

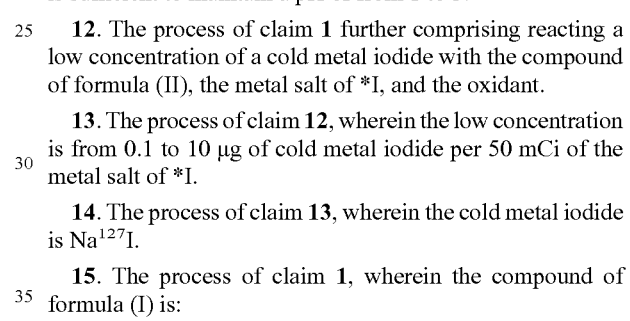

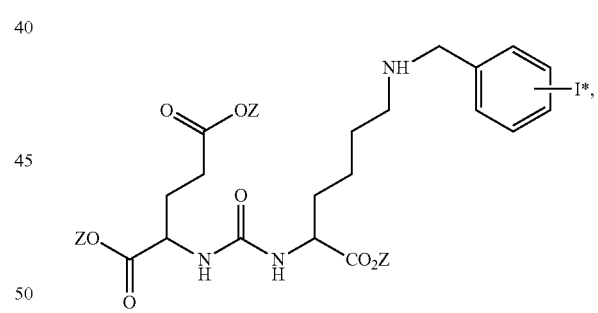

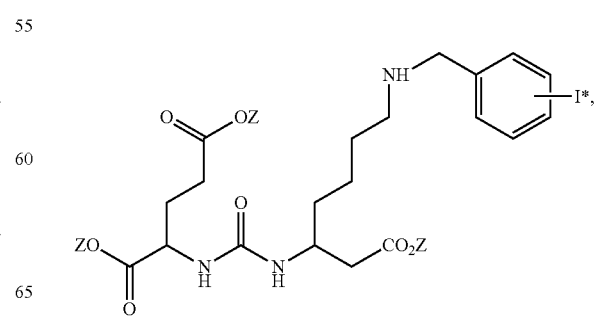

29
-continued

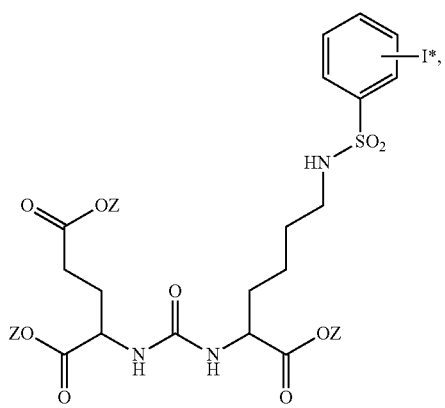

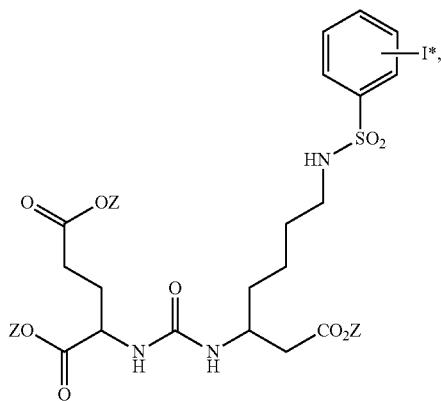

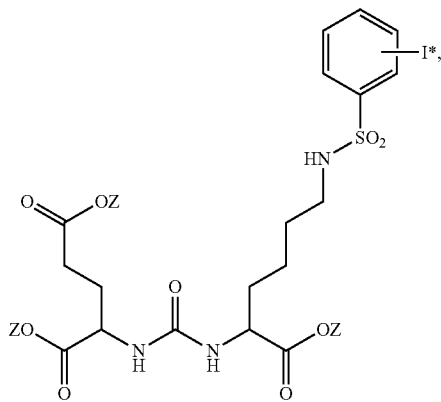

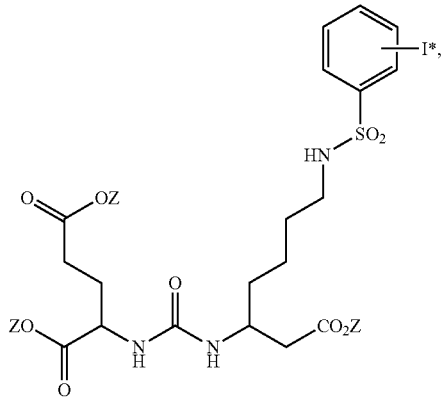

30
-continued

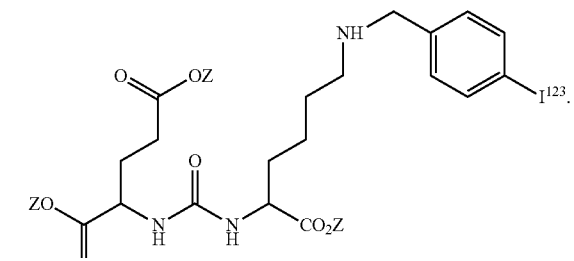

wherein:
*I is $^{123}$I, $^{124}$I, $^{125}$I or $^{131}$I; and
Z is H, $C_1$-$C_4$ alkyl, benzyl, substituted benzyl or tri-alkylsilyl.

16. The process of claim 15, wherein Z is tert-butyl.

17. The process of claim 1, wherein the compound of formula (I) is

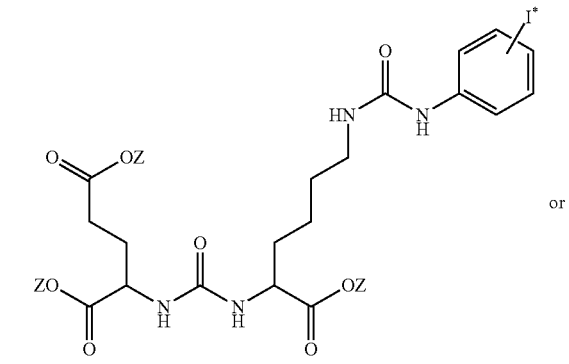

18. The process of claim 1 further comprising chromatographically purifying the radiolabeled compound of the formula (I).

19. The process of claim 18 further comprising adding 2-3% sodium gentisate and 5-6% ascorbate/asorbic acid at a pH of from 4.5 to 5.5 to stabilize the radiolabeled compound represented by formula (I).

20. A process for the preparation of a radiolabeled compound of formula:

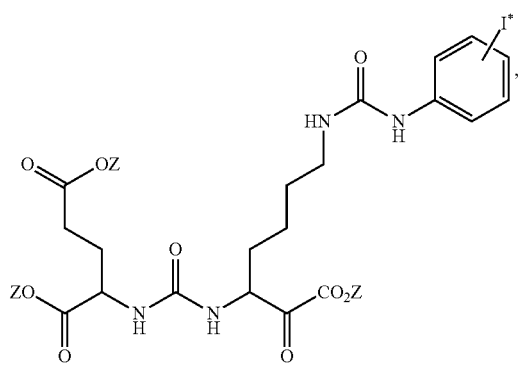

the process comprising:

reacting a compound of formula

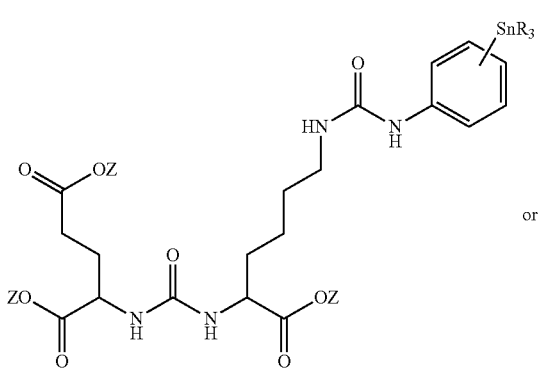

or

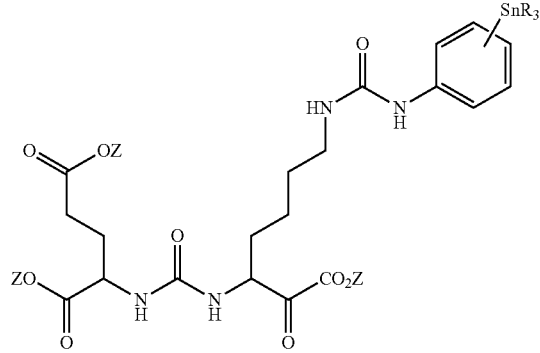

with a metal salt of *I in the presence of an oxidant under acidic conditions, wherein:

*I is $^{123}$I; $^{124}$I; $^{125}$I or $^{131}$I;

R is lower alkyl, optionally substituted with one or more fluorides; and

Z is H, $C_1$-$C_4$ alkyl, benzyl, substituted benzyl or trialkylsilyl.

21. The process of claim 20, wherein the acidic conditions comprise a pH of less than about 3.

22. The process of claim 20, wherein R is methyl.

23. The process of claim 20, wherein the metal salt of *I is a Group IA metal salt of *I wherein *I is $^{123}$I; $^{124}$I, $^{125}$I or $^{131}$I.

24. The process of claim 23, wherein the metal salt is a sodium salt.

25. The process of claim 20, wherein Z is H or $C_1$-$C_4$ alkyl.

26. The process of claim 20, wherein Z is tert-butyl.

27. The process of claim 20 further comprising chromatographically purifying the radiolabeled compound.

28. The process of claim 20 further comprising adding 2-3% sodium gentisate and 5-6% ascorbate/asorbic acid at a pH of from 4.5 to 5.5 to stabilize the radiolabeled compound.

* * * * *